United States Patent
Miyashita et al.

(10) Patent No.: US 9,476,808 B2
(45) Date of Patent: Oct. 25, 2016

(54) DEVICE FOR CAPTURING OBJECT AND METHOD FOR USING THE SAME

(75) Inventors: Noe Miyashita, Tokyo (JP); Koji Seo, Tokyo (JP); Matsuo Kamitani, Tokyo (JP)

(73) Assignee: HITACHI PLANT SERVICES CO., LTD., Tokyo (JP)

( * ) Notice: Subject to any disclaimer, the term of this patent is extended or adjusted under 35 U.S.C. 154(b) by 1010 days.

(21) Appl. No.: 12/977,860

(22) Filed: Dec. 23, 2010

(65) Prior Publication Data
US 2011/0159536 A1 Jun. 30, 2011

(30) Foreign Application Priority Data

Dec. 25, 2009 (JP) .................................. 2009-295655

(51) Int. Cl.
*G01N 1/22* (2006.01)
*C12M 1/34* (2006.01)

(52) U.S. Cl.
CPC ............ *G01N 1/2273* (2013.01); *C12M 41/36* (2013.01)

(58) Field of Classification Search
CPC .... C12M 25/02; C12M 33/14; C12M 37/02; C12M 27/02; C12M 35/04; C12M 21/04; C12M 23/14; C12M 29/10; B01D 24/10; B01D 24/20; B01D 25/02; C12Q 1/04; C12Q 1/045; C12Q 1/10; C12Q 1/18; C12Q 1/134
USPC ................................................ 435/34, 283.1
See application file for complete search history.

(56) References Cited

U.S. PATENT DOCUMENTS

| | | | |
|---|---|---|---|
| 3,001,914 | A | 9/1961 | Andersen |
| 3,400,575 | A | 9/1968 | Madden |
| 5,471,994 | A | 12/1995 | Guirguis |
| 5,635,349 | A | 6/1997 | LaMarco et al. |
| 2002/0066321 | A1 | 6/2002 | Lagraff et al. |
| 2003/0075048 | A1 | 4/2003 | Jordan et al. |
| 2005/0058575 | A1 | 3/2005 | Ishikawa et al. |
| 2009/0142785 | A1 | 6/2009 | Osato et al. |
| 2011/0183371 | A1 | 7/2011 | Noda et al. |

FOREIGN PATENT DOCUMENTS

| | | | |
|---|---|---|---|
| EP | 0 636 873 A1 | 7/1994 | |
| EP | 636873 A1 * | 2/1995 | ............... G01N 1/24 |

(Continued)

OTHER PUBLICATIONS

EP Search Report of Appln. No. 10015991.2 dated Feb. 9, 2012 in English.
Singapore Written Opinion and Search Report of Appln. 201009593-3 dated Jan. 31, 2012 in English.
Office action of Chinese Appln. No. 201010606111.9 dated Dec. 4, 2012 with English translation.

(Continued)

*Primary Examiner* — Michael Hobbs

(57) ABSTRACT

An object of the present invention is to provide an object-capturing device which accurately detects objects such as microorganisms captured at a test site. The object-capturing device of the present invention includes a capturing dish holding a carrier, which captures objects (microorganisms), on a first side of the capturing dish. The capturing dish has a through hole extending from the first side to a second side of the capturing dish. The object-capturing device is used in a way such that, after the objects are captured with the carrier directed upward, the carrier is directed downward and reagents for detecting the objects are contacted with the objects captured on the carrier through the through hole.

2 Claims, 9 Drawing Sheets

(56) References Cited

FOREIGN PATENT DOCUMENTS

| | | |
|---|---|---|
| EP | 1 517 129 | 3/2005 |
| EP | 2 305 789 | 4/2011 |
| JP | 06-063132 | 3/1994 |
| JP | 10-510429 | 10/1998 |
| JP | 11-137293 | 5/1999 |
| JP | 2005-91118 | 4/2005 |
| JP | 2005-091118 | 4/2005 |
| JP | 2009-131186 | 6/2009 |
| WO | WO 96/17084 | 6/1996 |
| WO | WO 2005/008244 A1 | 1/2005 |
| WO | WO 2009/157510 | 12/2009 |
| WO | WO 2009/157510 A1 | 12/2009 |

OTHER PUBLICATIONS

Notification of Reasons for Refusal dated Aug. 30, 2011.
EP Search Report of Appln. 10015991.2 dated Nov. 2, 2011 in English.
JP Notification of Reasons for Refusal of Appln. No. 2009-295655 dated Aug. 30, 2011 with English translation.
Search Report and Written Opinion from Singapore divisional appln. No. 201203492-2 dated Nov. 13, 2013 in English.
Search Report and Written Opinion from Singapore divisional appln. No. 201203491-4 dated Nov. 13, 2013 in English.
EP Search Report of Appln. No. 13004833.3 dated Dec. 3, 2013 in English.
Third Office Action of Chinese Patent Appln. No. 201010606111.9 dated Nov. 27, 2013 with English translation.

* cited by examiner

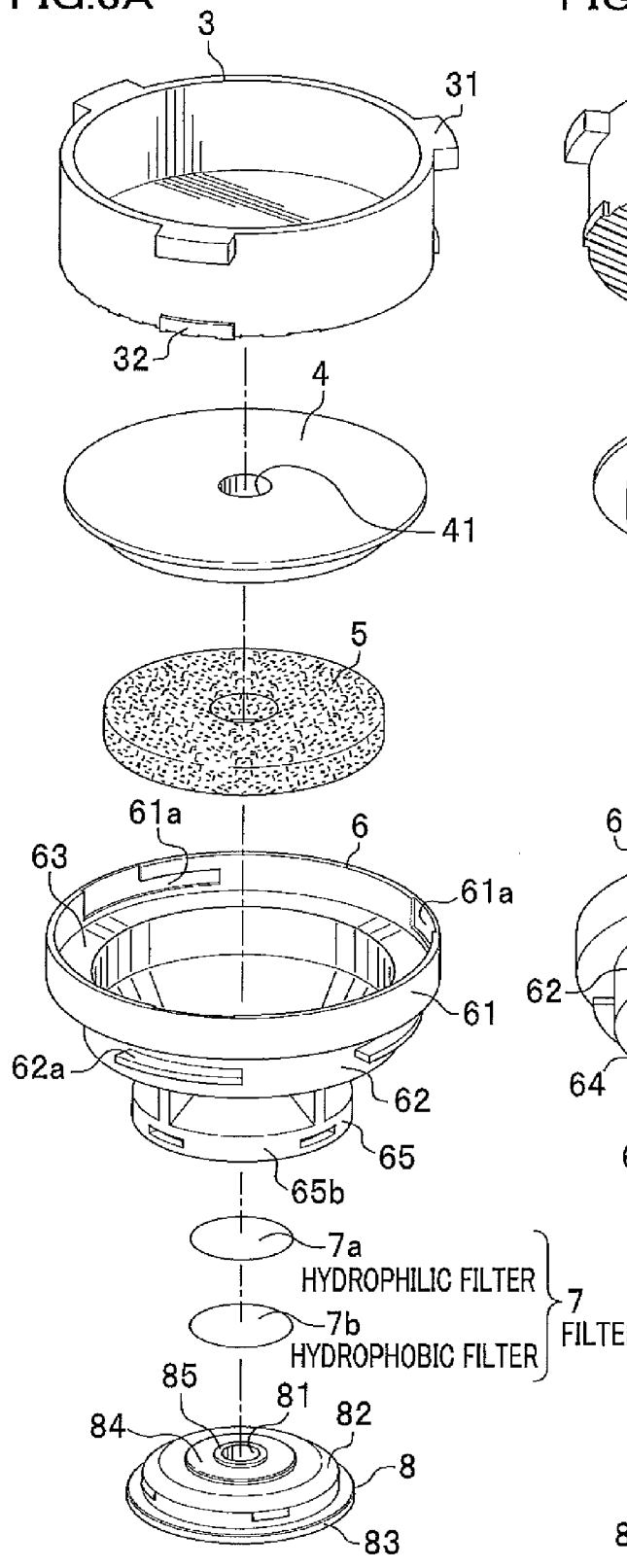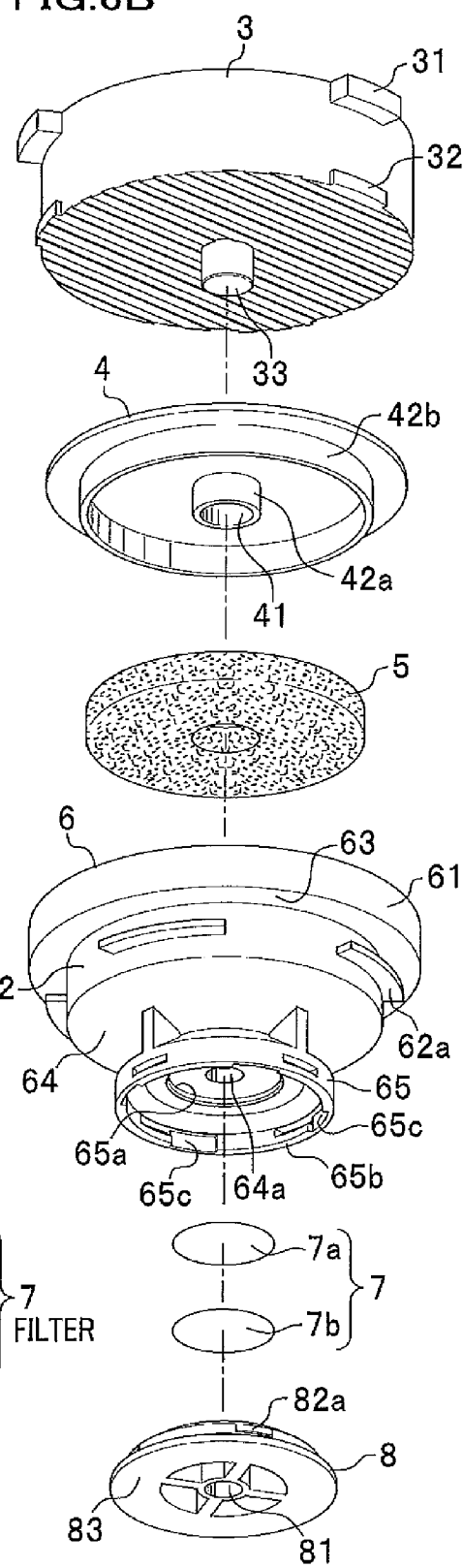

FIG.9A1
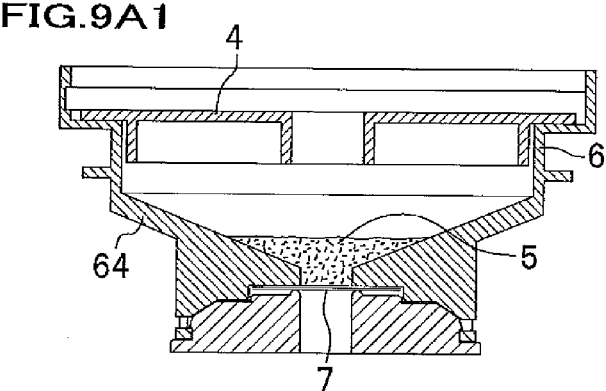
FIG.9B1
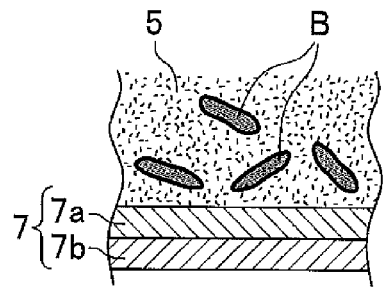
FIG.9A2
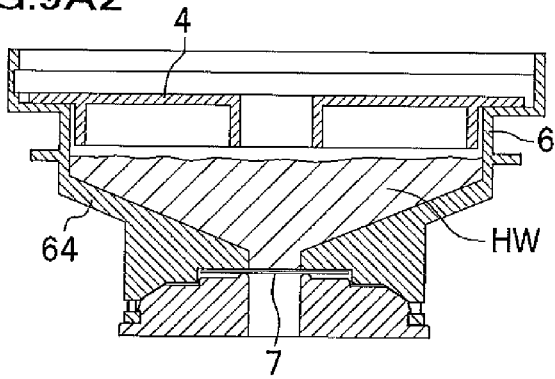
FIG.9B2
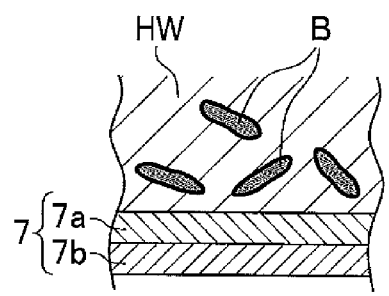
FIG.9A3
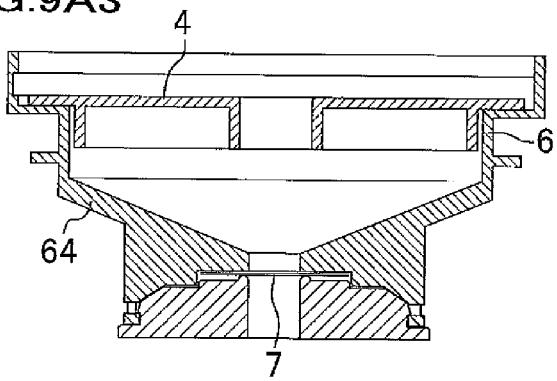
FIG.9B3
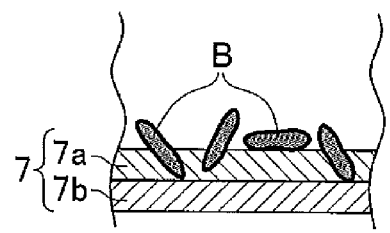
FIG.9A4
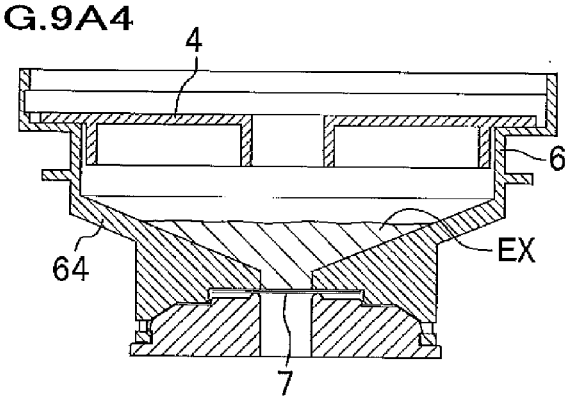
FIG.9B4
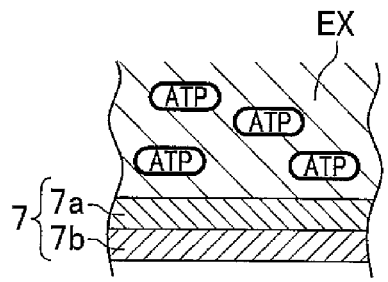

DEVICE FOR CAPTURING OBJECT AND METHOD FOR USING THE SAME

CROSS-REFERENCE TO RELATED APPLICATION

The present application claims priority under 35 USC 119 to Japanese Patent Application No. 2009-295655 filed on Dec. 25, 2009 the entire contents of which are hereby incorporated by reference.

BACKGROUND OF THE INVENTION

1. Field of the Invention

The present invention relates to an object-capturing device, which captures objects, such as microorganisms and chemical substances, in the air, and a method for using the object-capturing device.

2. Description of the Related Art

Conventionally, a technique of capturing objects, such as air-borne microorganisms and chemical substances, by sucking air through a filter and separating the objects by the filter has been well-known. A well-known capturing device for capturing air-borne microorganisms has a carrier, which undergoes a phase transition from gel to sol at a temperature raised from room temperature, on a capturing dish, as disclosed in, for example, Japanese Patent Application Laid-Open No. 2009-131186. Such capturing device is attached to an impactor-type air sampler. When air sucked by the air sampler collides with the carrier, microorganisms carried by the air flow are captured by the carrier in a gel phase. The carrier solates by raising the temperature, and thereby the captured microorganisms with the carrier in a sol phase are obtained from the capturing dish. The obtained microorganisms are counted according to a predetermined counting method.

A well-known method for counting microorganisms is the ATP method, which quantifies adenosine triphosphates (ATPs) extracted from microorganisms and thereby counts the microorganisms, as disclosed in, for example, Japanese Patent Application Laid-Open No. 11-137293. The ATP method extracts ATPs contained in the microorganisms by contacting the captured microorganisms with an ATP extracting reagent, and counts the microorganisms based on the intensity of luminescence measured when the extracted ATPs reacts with a luminescence reagent.

For example, a method for counting captured microorganisms based on the number of microorganism colonies cultured in a plate medium requires several days. On the other hand, the ATP method requires about one to several hours from the capturing of microorganisms to the counting of the microorganisms. Thus, the ATP method dramatically reduces the required time.

However, the ATP method counts microorganisms based on weak luminescence intensity. Substances that act as disturbance factors may be contained in a sample to be counted. Consequently, these substances need to be minimized.

A conventional capturing device, such as a device disclosed in Japanese Patent Application Laid-Open No. 2009-131186, has a carrier exposed on a capturing dish. Thus, for example, microorganisms other than those to be tested, or other substances that act as disturbance factors may attach onto the exposed carrier during the time after microorganisms are captured onto the carrier in an air sampler and before the microorganisms are counted. Particularly, when a test site where microorganisms are captured is far from a site where the microorganisms are counted, the carrier may be more heavily contaminated.

In other words, when the capturing device, such as the device disclosed in Japanese Patent Application Laid-Open No. 2009-131186, is used, the carrier is contaminated during the time after the carrier is removed from the air sampler and before the microorganisms are counted, and thereby the microorganisms captured at the test site may not be accurately counted.

SUMMARY OF THE INVENTION

An object of the present invention is to provide an object-capturing device and a using method thereof which accurately detect objects such as microorganisms captured at a test site.

To solve the above problems, the present invention provides an object-capturing device which includes a capturing dish holding a carrier, which captures an object, on a first side of the capturing dish. The capturing dish has a through hole extending from the first side to a second side of the capturing dish.

To solve the above problems, the present invention also provides a method for using the object-capturing device. The object-capturing device includes a carrier capturing an object, and a capturing dish holding the carrier on a first side of the capturing dish, and the capturing dish has a through hole extending from the first side to a second side of the capturing dish. The method includes the successive steps of; directing the carrier upward and capturing the object; and directing the carrier downward and contacting a reagent for detecting the object with the object captured on the carrier through the through hole.

BRIEF DESCRIPTION OF THE DRAWINGS

FIG. 6A is an exploded perspective view showing the object-capturing device of FIG. 5 viewed from obliquely above;

FIG. 6B is an exploded perspective view showing the object-capturing device of FIG. 5 viewed from obliquely below;

FIG. 9A1 is a cross-sectional view of the object-capturing device, showing a method for using the object-capturing device in the microorganism counting apparatus;

FIG. 9A2 is a cross-sectional view of the object-capturing device, showing the method for using the object-capturing device in the microorganism counting apparatus;

FIG. 9A3 is a cross-sectional view of the object-capturing device, showing the method for using the object-capturing device in the microorganism counting apparatus;

FIG. 9A4 is a cross-sectional view of the object-capturing device, showing the method for using the object-capturing device in the microorganism counting apparatus;

FIG. 9B1 is an enlarged schematic diagram showing the vicinity of a filter in the case of FIG. 9A1;

FIG. 9B2 is an enlarged schematic diagram showing the vicinity of the filter in the case of FIG. 9A2;

FIG. 9B3 is an enlarged schematic diagram showing the vicinity of the filter in the case of FIG. 9A3; and FIG. 9B4 is an enlarged schematic diagram showing the vicinity of the filter in the case of FIG. 9A4.

DETAILED DESCRIPTION OF THE PREFERRED EMBODIMENT

An object-capturing device according to an embodiment of the present invention will be described in detail with reference to the drawings as appropriate. The embodiment will be described using an object-capturing device for capturing air-borne microorganisms (for example, microbes and fungi) as an example. However, the objects captured by the object-capturing device of the present invention may be microscopic particles of metal or of chemical substances. The objects are not limited to solid objects, and may be mist.

First, an overall structure of a microorganism counting apparatus having the object-capturing device mounted therein, and a method for counting microorganisms with the microorganism counting apparatus will be described according to the embodiment. Second, the object-capturing device and a method for using the object-capturing device will be described according to the embodiment.

Overall Structure of Microorganism Counting Apparatus

Figure 1:
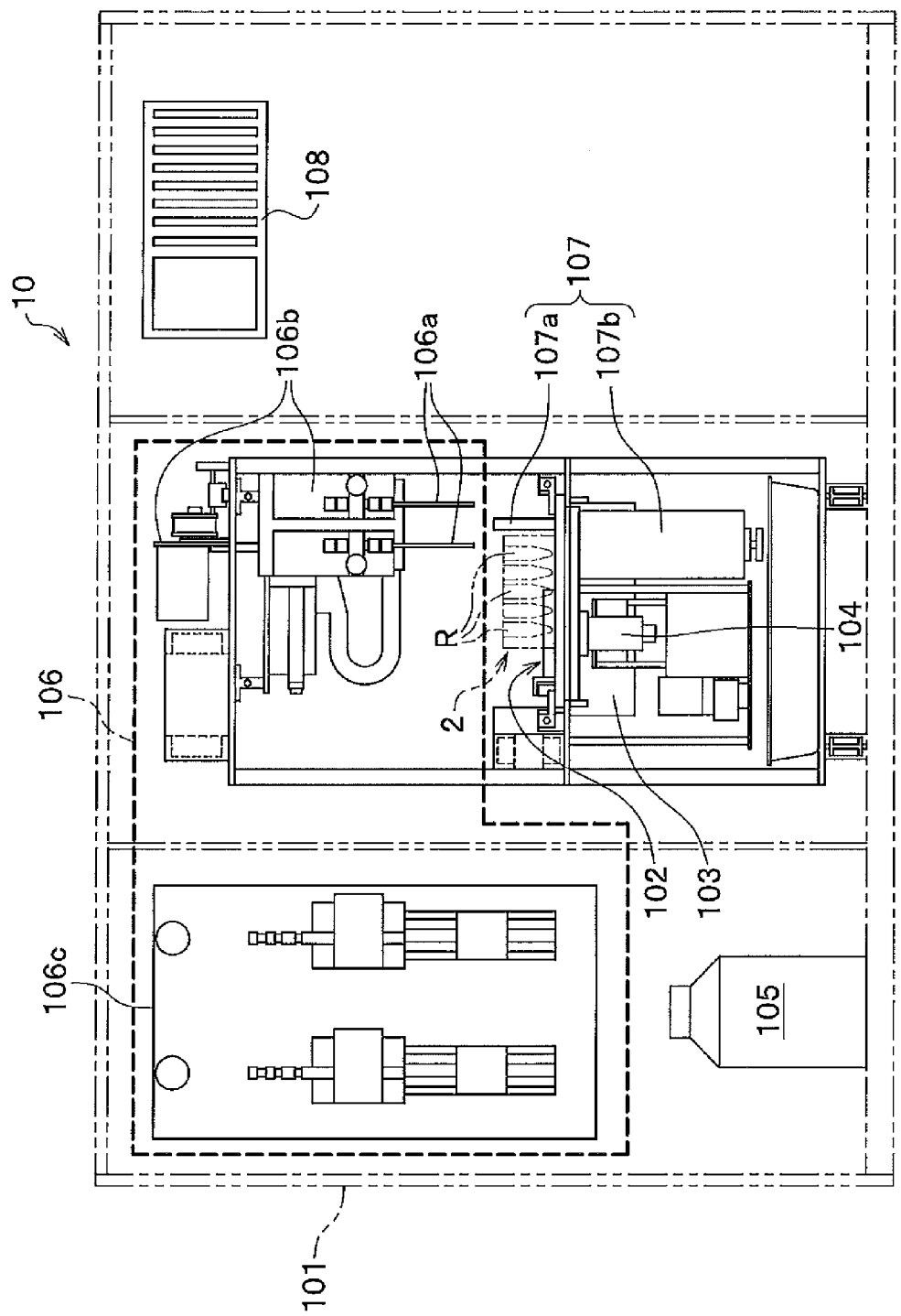
FIG. 1 is a diagram showing a structure of a microorganism counting apparatus having an object-capturing device mounted therein according to an embodiment of the present invention.

As shown in FIG. 1, a microorganism counting apparatus 10 is an apparatus for counting microorganisms contained in a sample according to the ATP method. The microorganism counting apparatus 10 includes a mounting unit 102 mounting an object-capturing device 1 (refer to FIG. 2) having the sample therein, a functional liquid tank 105, a hot-water supplying unit 103, a suction unit 104, a reagent cartridge 2 having multiple reagents R, a dispensing unit 106, a luminescence-intensity measurement unit 107, and a control unit 108, which are housed in a cabinet 101.

For simplicity, FIG. 1 shows the cabinet 101 and the reagent cartridge 2 in a dashed-two-dotted line, and omits the object-capturing device 1.

Figure 2:
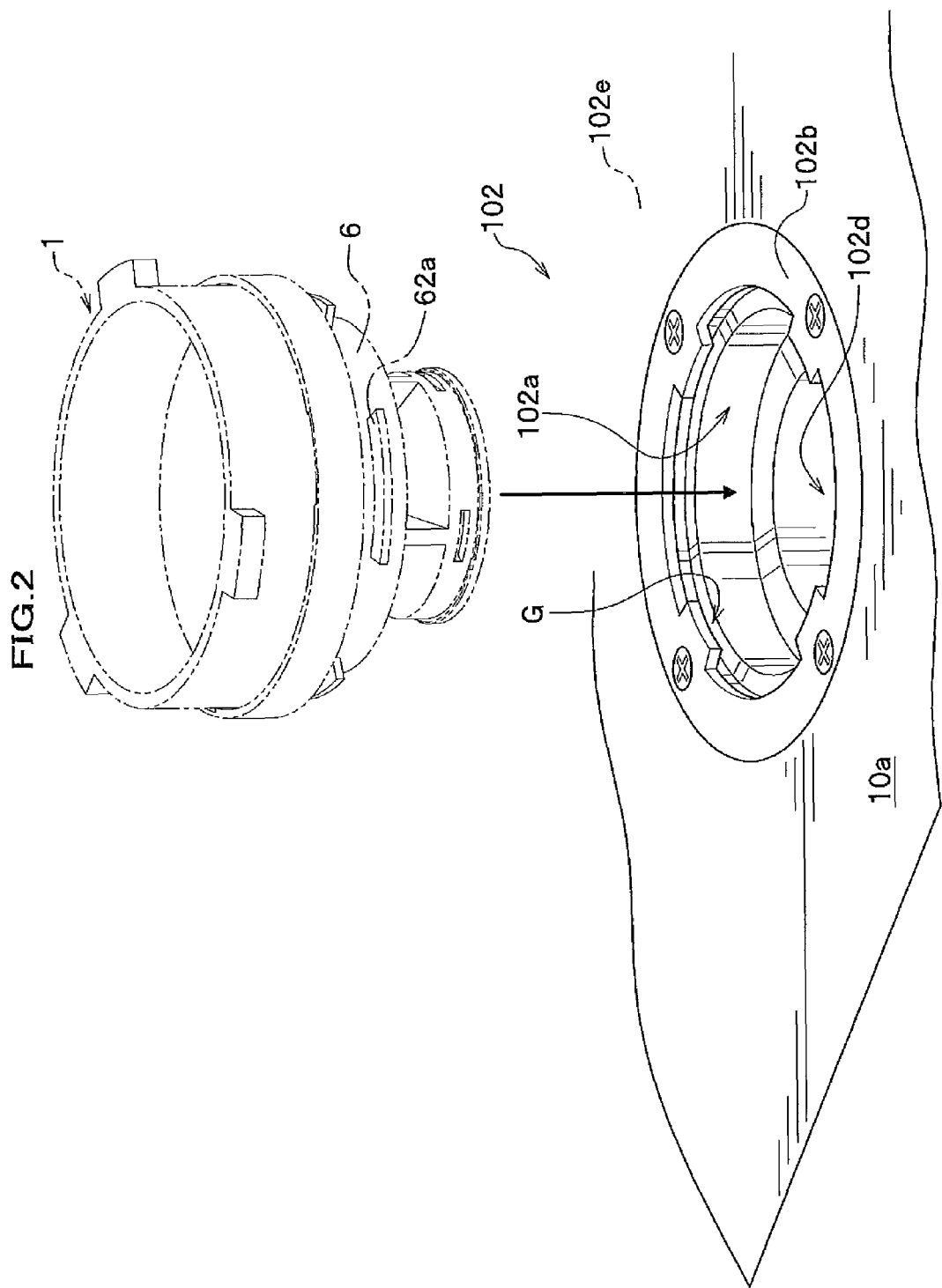
FIG. 2 is a perspective view showing the vicinity of a mounting unit for the object-capturing device in the microorganism counting apparatus of FIG. 1.

As shown in FIG. 2, the mounting unit 102 has a recessed portion 102a receiving the object-capturing device 1 (i.e., a housing 6). The mounting unit 102 also includes an engaging ring 102b. As described below, a heater 102c (refer to FIG. 3) is embedded in an aluminum member surrounding the recessed portion 102a, that is, forming the recessed portion 102a. To form the recessed portion 102a, other highly heat conductive members may be used instead of the aluminum member.

The engaging ring 102b is attached on the periphery of the opening of the recessed portion 102a. As described in detail below, the housing 6 is mounted on the mounting unit 102 by engaging the engaging ring 102b with first engaging claws 62a provided on the housing 6 of the object-capturing device 1. The engaging ring 102b has cutout portions 102d in such a planar shape as to receive respective first engaging claws 62a of the housing 6. Between the engaging ring 102b and an apparatus body 10a having the recessed portion 102a formed therein, a gap G is formed to have a height large enough for receiving the first engaging claws 62a.

In other words, when the housing 6 is fitted into the recessed portion 102a, the first engaging claws 62a are inserted into the recessed portion 102a through respective cutout portions 102d, and the housing 6 is rotated to slide the first engaging claws 62a into the gap G. Thereby, the housing 6 is engaged with the engaging ring 102b.

Figure 3:
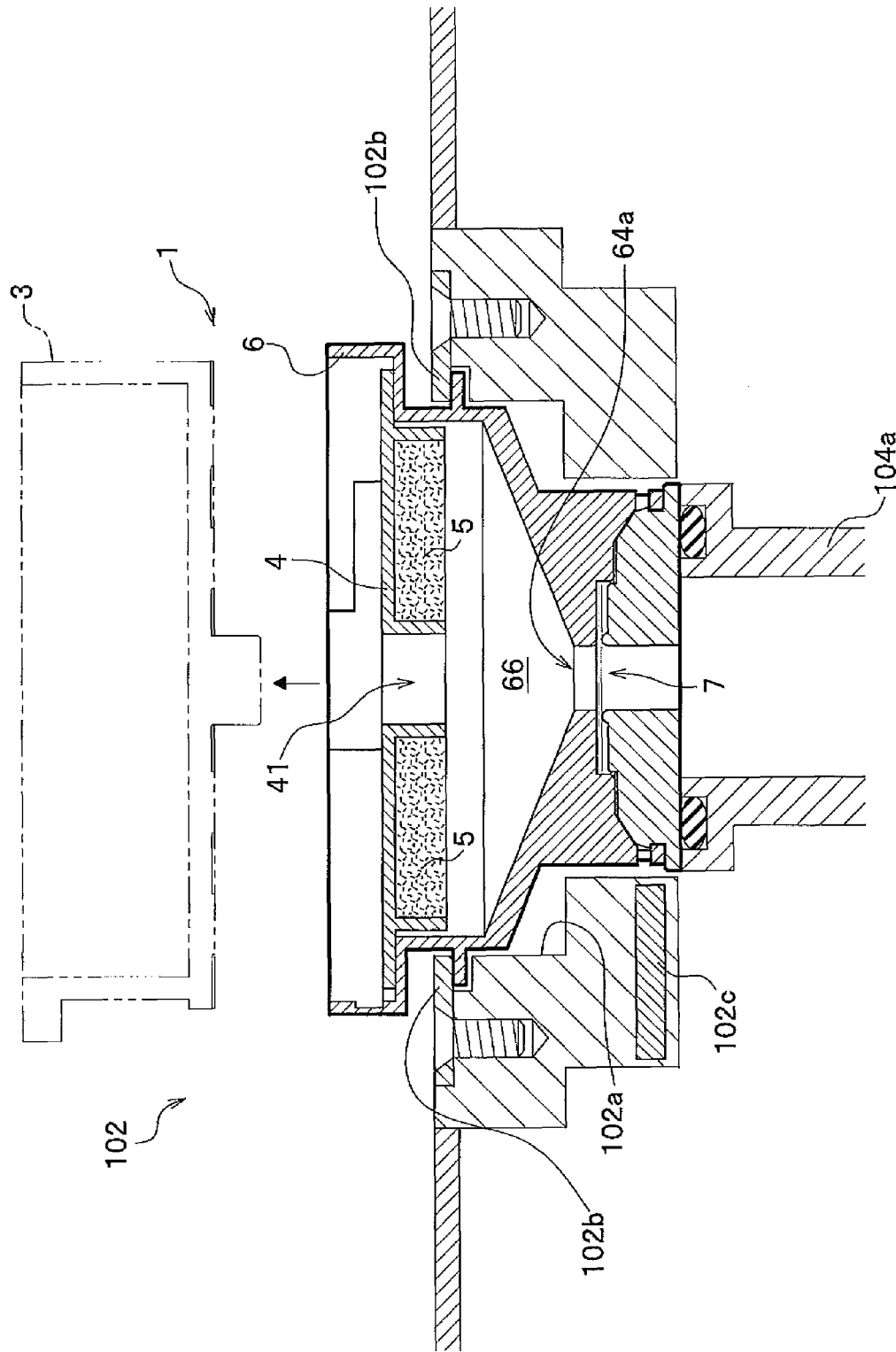
FIG. 3 is a cross-sectional view showing the object-capturing device mounted on the mounting unit in the microorganism counting apparatus of FIG. 1.

As shown in FIG. 3, when the object-capturing device 1 is placed in the recessed portion 102a, a cover 3 of the object-capturing device is removed, and a capturing dish 4 disposed in the housing 6 is exposed, as described in detail below.

In FIG. 3, a through hole 41 for injecting the reagents R (refer to FIG. 1) and hot water into an internal space 66 of the housing 6, a carrier 5 disposed on the back side of the capturing dish 4, a discharge opening 64a of the housing 6, a filter 7 provided on the outside of the discharge opening 64a, and a suction head 104a of the suction unit 104 (refer to FIG. 1) connected with the housing 6 are shown. The internal space 66 corresponds to "a space" in the claims.

As shown in FIG. 3, the object-capturing device 1 is mounted on the mounting unit 102 through the engaging ring 102b. In the object-capturing device 1, the capturing dish 4 having the through hole 41 is disposed above the housing 6, and the carrier 5 as a sample is disposed on the back side of the capturing dish 4 and in the internal space 66 of the housing 6.

In the object-capturing device 1 mounted on the mounting unit 102, the housing 6 has a protruding portion which protrudes upward from the recessed portion 102a, and the capturing dish 4 is disposed in the protruding portion. The heater 102c may be any means that is capable of heating the recessed portion 102a (the aluminum member), which surrounds the housing 6 of the object-capturing device 1 mounted on the mounting unit 102, to a predetermined temperature. Specifically, the heater 102c is preferable to be, for example, a cartridge heater.

The functional liquid tank 105 shown in FIG. 1 is adapted to store liquid such as sterile distilled water. This liquid is poured into the housing 6 (refer to FIG. 3) to, for example, improve a filtration rate of the carrier 5 (refer to FIG. 3) of the object-capturing device 1, or to wash the housing, as described below. The liquid is also poured into a piping system connected to a syringe pump 106c of the dispensing unit 106 as described below. The functional liquid tank 105 may store buffer solution.

The hot-water supplying unit 103 heats and supplies, for example, the sterile distilled water supplied from the functional liquid tank 105. Specifically, the hot-water supplying unit 103 injects hot water into the internal space 66 (refer to FIG. 3) in the housing 6 through the through hole 41 (refer to FIG. 3) of the capturing dish 4. For example, the hot-water supplying unit 103 is a unit (not shown) for discharging hot water heated by a cartridge heater with a peristaltic pump through a nozzle formed with, for example, a flexible tube. This nozzle having a means for moving in horizontal and vertical directions is inserted into the internal space 66 (refer to FIG. 3) of the housing 6 through the through hole 41 (refer to FIG. 3) of the capturing dish 4 as necessary.

The suction unit 104 shown in FIG. 1 sucks, for example, the hot water and the reagents R described below, which are injected into the internal space 66 (refer to FIG. 3) in the housing 6, to discharge them through the filter 7 (refer to FIG. 3). For example, this suction unit 104 includes the suction head 104*a* (refer to FIG. 3) described above, a suction pump (not shown) connected with the suction head 104*a* through predetermined piping, and a waste tank.

The suction unit 104 according to the embodiment further includes a lifting apparatus (not shown) lifting and lowering the suction head 104*a* to enable the suction head 104*a* (refer to FIG. 3) to be engaged with and disengaged from the housing 6 (refer to FIG. 3) mounted on the mounting unit 102.

In the reagent cartridge 2 shown in FIG. 1, multiple reagents R necessary to the ATP method are arranged in a block. The reagent cartridge 2 is disposed at a predetermined position in the vicinity of the mounting unit 102. In the reagent cartridge 2, each reagent R is disposed at a predetermined position, and a dispensing nozzle 106*a* of the dispensing unit 106 described below dispenses the reagents R in a predetermined order into the housing 6 of the object-capturing device 1 and into a luminescence-test tube 107*a* of the luminescence-intensity measurement unit 107. In other words, the location (the coordinates) of each reagent R is stored in the control unit 108 controlling the dispensing unit 106, as described below.

Examples of the reagents R necessary to the ATP method includes an ATP eliminating reagent for eliminating ATPs that exist out of cells of captured microorganisms, an ATP extracting reagent for extracting ATPs contained in the microorganisms, and an ATP luminescence reagent for producing luminescence of the ATPs extracted from the microorganisms.

Examples of the ATP eliminating reagent include an ATP-degrading enzyme.

Examples of the ATP extracting reagent include a benzalkonium chloride, a trichloroacetic acid, and a Tris buffer solution.

Examples of the ATP luminescence reagent include a luciferase/luciferin reagent.

The examples of the reagents R may include a correction reagent for the luminescence-intensity measurement unit 107, and sterile pure water.

The dispensing unit 106 shown in FIG. 1 dispenses the reagents R described above into the housing 6 of the object-capturing device 1. The dispensing unit 106 also dispenses the reagents R and ATP extracted solution in the housing 6 (refer to FIG. 3) as described below into the luminescence-test tube 107*a* of the luminescence-intensity measurement unit 107.

The dispensing unit 106 may include the dispensing nozzle 106*a* formed with a thin tube, an actuator 106*b* moving the dispensing nozzle 106*a* in the xyz axis directions, the syringe pump 106*c* connected with the dispensing nozzle 106*a* through predetermined flexible piping, the piping (not shown) supplying, for example, sterile distilled water from the functional liquid tank 105 through the syringe pump 106*c* to the dispensing nozzle 106*a*.

The luminescence-intensity measurement unit 107 shown in FIG. 1 may be a unit which includes the luminescence-test tube 107*a* for receiving the ATP extracted solution dispensed from the housing 6 (refer to FIG. 3) as described below to produce luminescence of ATPs, and a luminescence detecting unit body 107*b* having, for example, a photomultiplier which detects luminescence intensity of the ATPs.

The control unit 108 shown in FIG. 1 has overall control over the microorganism counting apparatus 10. The control unit 108 also controls the hot-water supplying unit 103, the suction unit 104, the dispensing unit 106, and the luminescence-intensity measurement unit 107 according to a procedure to be described below, after the object-capturing device 1 (refer to FIG. 3) is mounted on the mounting unit 102. This control unit 108 includes a CPU, a ROM, a RAM, various interfaces, and circuitry.

Figure 4:
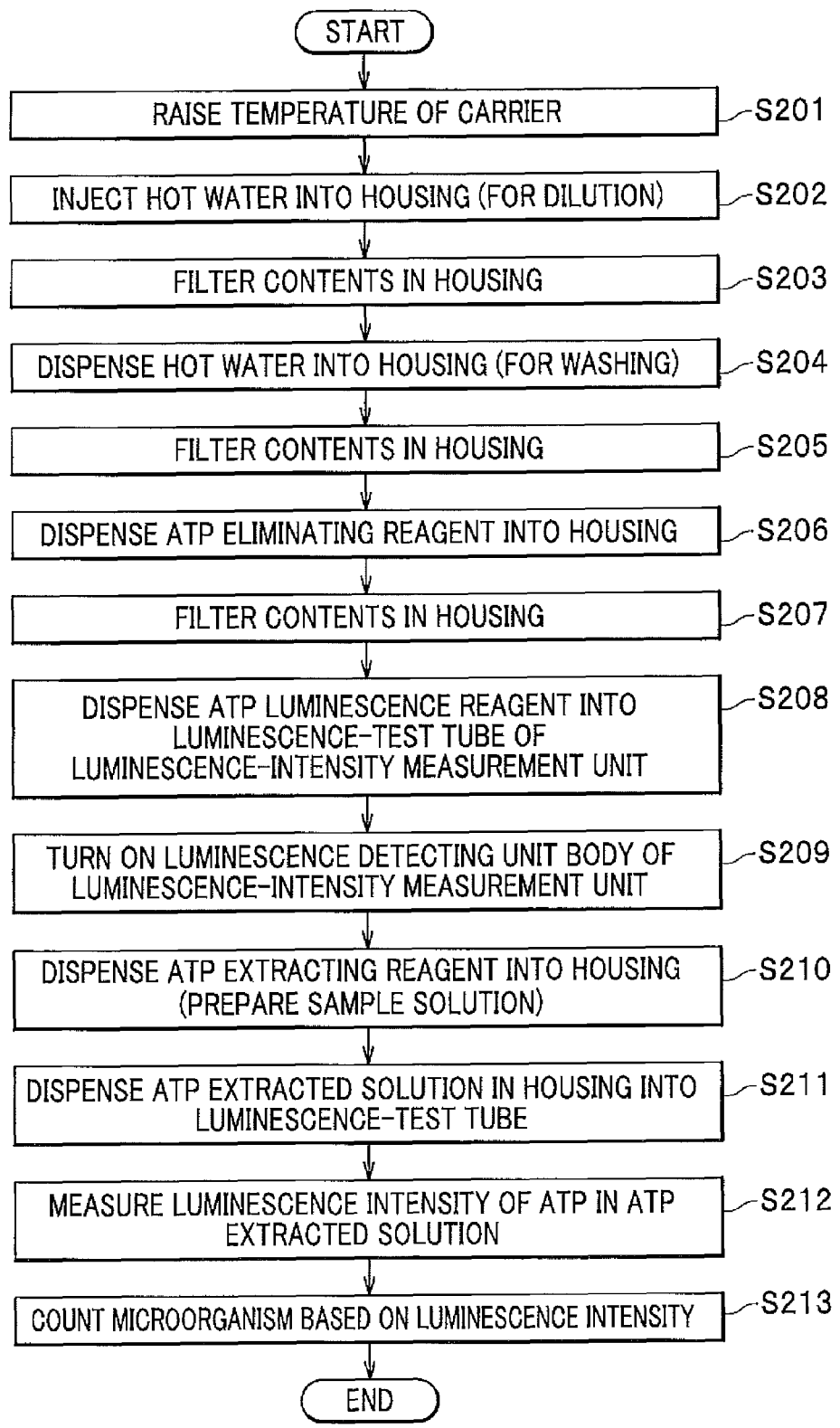
FIG. 4 is a flowchart of operations of the microorganism counting apparatus based on instructions of a control unit.

Operations of Microorganism Counting Apparatus and Method for Counting Microorganisms A procedure of execution by the control unit 108 will be described. In this description, operations of the microorganism counting apparatus 10 and a method for counting microorganisms will be described. FIG. 4, which is referred to in the following description, is a flowchart showing the procedure in which the microorganism counting apparatus operates based on instructions of the control unit.

In the microorganism counting apparatus 10 shown in FIG. 1, the control unit 108 starts execution of the following procedure when a start switch (not shown) is turned on after the object-capturing device 1 (refer to FIG. 3) is mounted on the mounting unit 102.

As shown in FIG. 4, the control unit 108 sends an instruction to, for example, a predetermined inverter to apply power to the heater 102*c* (refer to FIG. 3) to generate heat. On the request of the control unit 108, the temperature of the carrier 5 (refer to FIG. 3) of the object-capturing device 1 is raised with the heater 102*c* (Step S201). Thereby, the carrier 5 solates and falls down off the capturing dish 4 (refer to FIG. 3) onto the inside bottom of the housing 6 (refer to FIG. 3).

The control unit 108 sends an instruction to the hot-water supplying unit 103 (refer to FIG. 1) to inject hot water into the housing 6 (refer to FIG. 3) (Step S202). Thereby, the carrier 5 (refer to FIG. 3) further solates, and is diluted with the hot water.

The control unit 108 sends an instruction to the suction unit 104 (refer to FIG. 1) to engage the suction head 104*a* (refer to FIG. 3) with the housing 6 (refer to FIG. 3), and then suck and filter the contents in the housing 6 (refer to FIG. 3) (Step S203). Thereby, the microorganisms captured in the carrier 5 are separated and held by the filter 7 (refer to FIG. 3), and the diluted carrier 5 is filtered and discharged out of the housing 6.

The control unit 108 again sends an instruction to the hot-water supplying unit 103 to dispense hot water into the housing 6 (refer to FIG. 3) (Step S204). Then, the hot water in the housing 6 is filtered again (Step S205). Thereby, the filtered hot water removes remaining diluted carrier 5 from the inside of the housing 6, and accordingly the recovery rate of microorganisms at the filter 7 is improved.

The control unit 108 sends to an instruction to the dispensing unit 106 (refer to FIG. 1) to dispense the ATP eliminating reagent in the reagent cartridge 2 into the housing 6 (refer to FIG. 3) (Step S206). As a result, the ATPs that exist out of the cells of the microorganisms on the filter 7 are eliminated.

The control unit 108 sends an instruction to the suction unit 104 (refer to FIG. 1) to suck the contents of the housing 6 (refer to FIG. 3) and filter the sucked contents (Step S207). Thereby, the microorganisms are separated and held by the filter 7 (refer to FIG. 3), and the ATP eliminating reagent and the hot water are filtered and discharged out of the housing 6.

The control unit 108 sends an instruction to the dispensing unit 106 (refer to FIG. 1) to dispense the ATP luminescence reagent in the reagent cartridge 2 into the luminescence-test tube 107*a* (refer to FIG. 1) (Step S208).

The control unit 108 sends an instruction to the luminescence-intensity measurement unit 107 (refer to FIG. 1) to turn on the luminescence detecting unit body 107*b* (refer to FIG. 1) (Step S209).

The control unit 108 sends an instruction to the dispensing unit 106 (refer to FIG. 1) to dispense the ATP extracting reagent in the reagent cartridge 2 into the housing 6 (refer to FIG. 3) (Step S210). Thereby, ATPs are extracted from the microorganisms held by the filter 7, and sample solution is prepared on the filter 7.

After Steps S208 and S209, the luminescence detecting unit of the luminescence-intensity measurement unit 107 performs a background measurement of the luminescence-test tube 107a with the ATP luminescence reagent.

The control unit 108 sends an instruction to the dispensing unit 106 (refer to FIG. 1) to dispense an adequate amount of the sample solution (i.e., the ATP extracted solution) in the housing 6 into the luminescence-test tube 107a where the background measurement has been performed (Step S211). Thereby, the ATP extracted solution reacts with the ATP luminescence reagent which has been dispensed in Step S208, and produces luminescence in the luminescence-test tube 107a.

The luminescence detecting unit body 107b (refer to FIG. 1) of the luminescence-intensity measurement unit 107 (refer to FIG. 1) detects the ATP luminescence and outputs signals. The control unit 108 digitizes the outputted signals, and measures luminescence intensity based on the single-photon counting method (Step S212). Then, the control unit 108 calculates the ATP amount (amol) in the ATP extracted solution dispensed into the luminescence-test tube 107a based on a prestored calibration curve indicating the relation between the ATP amount (amol) and the luminescence intensity (CPS), and the control unit 108 counts the microorganisms using an ATP value, which may be converted into the equivalent number of the microorganisms in the carrier 5. This ATP value is calculated based on the ATP amount (amol) and the amount of the ATP extracted solution of the sample solution prepared in Step S210 (Step S213).

Object-Capturing Device

Figure 5:
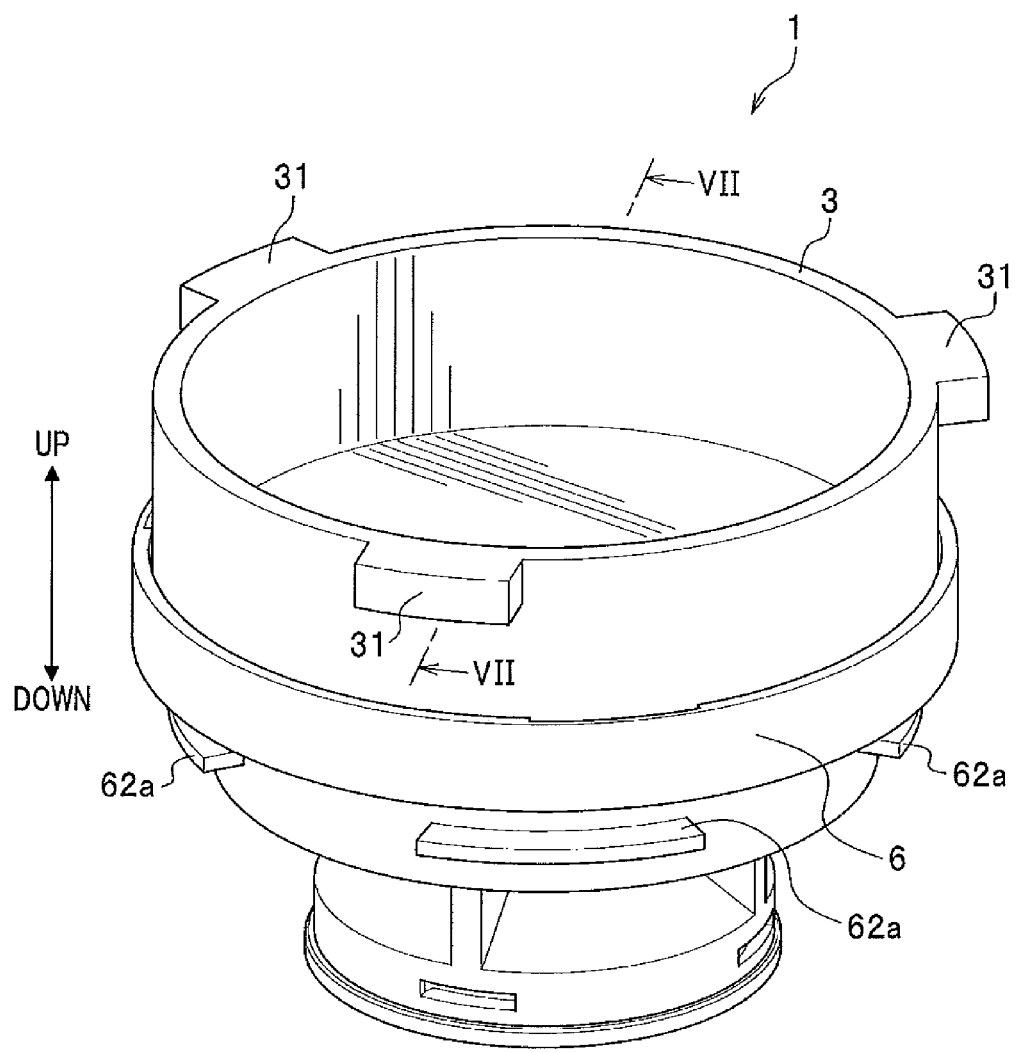
FIG. 5 is a perspective view showing the object-capturing device according to the embodiment.
Figure 7:
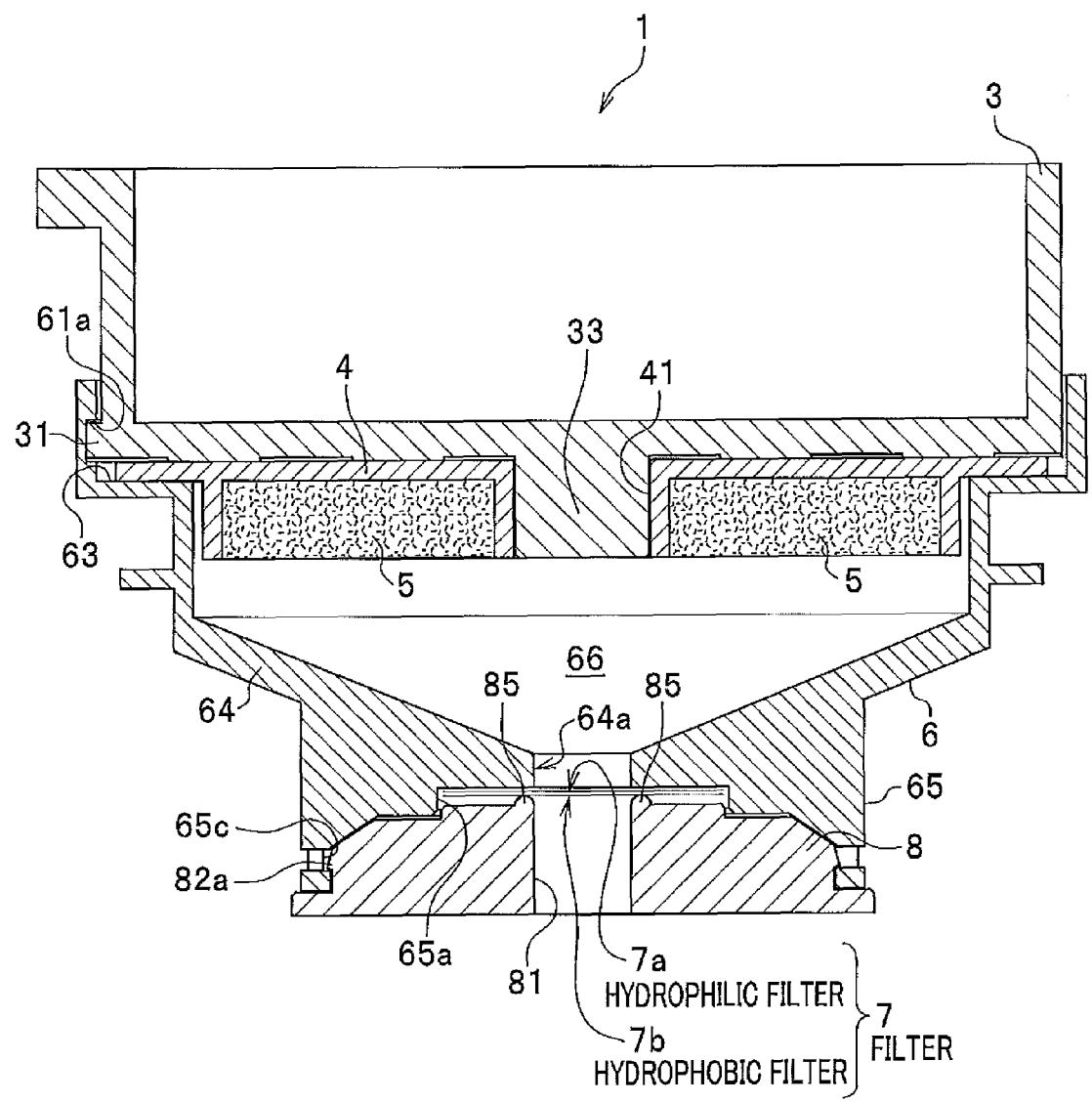
FIG. 7 is a cross-sectional view along a line VII-VII in FIG. 5.

The object-capturing device 1 according to the embodiment will be described. The up and down direction of the object-capturing device 1 in the following description is the same as that shown in FIG. 5. FIG. 5 is a perspective view showing the object-capturing device according to the embodiment. FIG. 6A is an exploded perspective view showing the object-capturing device of FIG. 5 viewed from obliquely above. FIG. 6B is an exploded perspective view showing the object-capturing device of FIG. 5 viewed from obliquely below. FIG. 7 is a cross-sectional view along a line VII-VII in FIG. 5.

The object-capturing device 1 according to the embodiment is placed in an impactor-type air sampler 50 (refer to FIG. 8) described below to capture microorganisms, which are air-borne objects. The object-capturing device 1 is mounted in the microorganism counting apparatus 10 described above to count the captured microorganism. The object-capturing device 1 is turned upside down and used when microorganisms are captured, as described in detail below.

As shown in FIG. 5, an upper portion of the object-capturing device 1 is in a substantially cylindrical shape, and a lower portion of the object-capturing device 1 is in a substantially conical shape so that the diameter of the horizontal cross section of the object-capturing device 1 becomes small downward as the horizontal cross section lowers. As described in detail below, the object-capturing device 1 is engaged with the air sampler 50 (refer to FIG. 8) in the upper portion of the object-capturing device 1 when microorganisms are captured. The object-capturing device 1 is engaged with the microorganism counting apparatus 10 in the lower portion of the object-capturing device 1 when the captured microorganisms are counted.

In FIG. 5, the cover 3, the housing 6, second engaging claws 31 engaging with the air sampler 50 (refer to FIG. 8) described below, and the first engaging claws 62a engaging with the microorganism counting apparatus 10 are shown. The air sampler 50 corresponds to "a capturing apparatus which captures the object" in the claims. Each second engaging claw 31 corresponds to "an engaging portion" in the claims.

As shown in FIGS. 6A and 6B, the object-capturing device 1 includes the cover 3, the capturing dish 4, the carrier 5, the housing 6, the filter 7, and a filter-securing ring 8, which are disposed in this order from upward to downward and fitted with each other.

The cover 3 is attached to close an upper opening of the housing 6 described below, and has a cylindrical shape with a bottom and an opening facing upward. On an upper circumferential edge of the outer cylindrical surface of the cover 3, the second engaging claws 31 described above are formed to protrude radially outward, and to be disposed in a constant spacing with each other on the circumferential surface of the cover 3. According to the embodiment, the number of the second engaging claws 31 is three, which is same as the number of engaging cutout portions 53 (refer to FIG. 8) described below of the air sampler 50.

On a lower circumferential edge of the outer cylindrical surface of the cover 3, three third engaging claws 32 are formed to protrude radially outward, and to be disposed in a constant spacing with each other on the circumferential surface of the cover 3. The third engaging claws 32 are fitted in respective first L-shaped grooves 61a described below of the housing 6 to detachably engage the cover 3 with the housing 6.

As shown in FIG. 6B, an outer bottom surface of the cover 3 forms an uneven surface constituted by multiple straight ridges and straight grooves disposed alternately and in parallel with each other, the ridges of which protrude downward. When the outer bottom surface of the cover 3 contacts with an upper surface of the capturing dish 4 as described below, this uneven outer bottom surface reduces the area of contact with the capturing dish 4. For example, after the object-capturing device 1 is mounted on the mounting unit 102 (refer to FIG. 2) of the microorganism counting apparatus 10 described above, when the cover 3 is removed from the housing 6, this uneven surface facilitates easy detachment of the cover 3 from the capturing dish 4 which is left in the housing 6. As described below, after microorganisms are captured using the air sampler 50 (refer to FIG. 8), when the object-capturing device 1 is carried to a microorganism counting facility (for example, a facility having the microorganism counting apparatus 10 (refer to FIG. 1)) at low temperature as necessary, condensation may rarely occur between the cover 3 and the capturing dish 4. Even in this case, the uneven surface facilitates easy detachment of the cover 3 from the capturing dish 4. This uneven surface is not limited to the above straight ridges and straight grooves, and may be formed with multiple protrusions, or with grains such as a matte finish pattern or a texture pattern.

As shown in FIG. 6B, on the outer bottom surface of the cover 3, a protrusion 33 in a cylindrical shape is formed to protrude downward. The protrusion 33 has an outer diameter rather smaller than the inner diameter of the through hole 41 of the capturing dish 4 to be described below. The height of the protrusion 33 equals to that of the through hole 41.

As shown in FIGS. 6A and 6B, the capturing dish 4 has a disk shape. The through hole 41, which is bored through the capturing dish 4 in the vertical direction, is formed in a center portion of the capturing dish 4.

As shown in FIG. 6A, the upper surface of the capturing dish 4 forms an even surface to be made in contact with the outer bottom surface of the cover 3 described above.

On a lower surface of the capturing dish 4, double ring-shaped ribs 42*a* and 42*b* extend vertically on the periphery of the through hole 41 in an inner portion and an outer portion, to receive the ring-shaped carrier 5 as described below.

The outer diameter of the capturing dish 4 ranges between the inner diameter of a lower cylinder portion 62 and the inner diameter of an upper cylinder portion 61 of the housing 6 (including both end values). Preferably, the outer diameter of the capturing dish 4 is substantially equal to the inner diameter of the upper cylinder portion 61. The outer diameter of the ring-shaped rib 42*b* formed in the outer portion of the capturing dish 4 shown in FIG. 6B is equal to the inner diameter of the lower cylinder portion 62 described below, or less. Preferably, the outer diameter of the ring-shaped rib 42*b* is substantially equal to the inner diameter of the lower cylinder portion 62.

The carrier 5 is placed in the air sampler 50 (refer to FIG. 8), as described below, to receive air flow when the air sampler 50 sucks the air, and to capture microorganisms carried in the air flow.

The carrier 5 is made of a material that undergoes a phase transition from gel to sol when the temperature rises from the room temperature. The material of the carrier 5 is preferably such a material as to undergoes a phase transition from gel to sol at 30° C. or higher. More preferably, the material liquefies at a temperature between 37° C. and 40° C. Most preferably, the material is a gelatin, a mixture of gelatin and glycerol, or a copolymer having a ratio of N-acryloylglycinamide to N-methacryloyl-N'-biotinyl propylene diamine of 10:1.

The carrier 5 has a ring shape, as described above. As shown in FIG. 6B, the carrier 5 preferably has the same shape as that of the space formed between the ring-shaped ribs 42*a* and 42*b* of the capturing dish 4.

The carrier 5 may be formed by applying the material described above to the space formed between the ring-shaped ribs 42*a* and 42*b*, or by filling the space with the material. Instead, a separated ring-shaped carrier may be fitted into the space.

As shown in FIGS. 6A and 6B, the housing 6 has the upper cylinder portion 61 having the inner diameter substantially as large as the outer diameter of the cover 3 as described above, the lower cylinder portion 62 having the inner diameter smaller than the inner diameter of the upper cylinder portion 61, a conical portion 64 being in an inverted conical shape with an inner diameter which becomes smaller from the inner diameter of the lower cylinder portion 62, and a filter fitting portion 65 provided on the periphery of an outlet of the discharge opening 64*a* formed in the lowest portion of the conical portion 64, which are disposed in this order from upward to downward to form an integral unit.

On an inner circumferential surface of the upper cylinder portion 61, three of the first L-shaped grooves 61*a*, into which the third engaging claws 32 of the cover are fitted, are formed at positions corresponding to the third engaging claws 32, as described above.

The lower cylinder portion 62 is connected with the upper cylinder portion 61 through a shelf portion 63.

On an outer circumferential surface of the lower cylinder portion 62, the first engaging claws 62*a* are formed to be engaged with engaging ring 102*b* (refer to FIG. 2) of the microorganism counting apparatus 10 described above. The first engaging claws 62*a* protrude outward in the radial direction of the lower cylinder portion 62, and are disposed in a constant spacing with each other on the circumferential surface of the lower cylinder portion 62. According to the embodiment, the number of the first engaging claws 62*a* is four.

The conical portion 64 having the inner diameter becoming smaller downward enables the contents to easily flow down toward the lowest portion, that is, the discharge opening 64*a* (refer to FIG. 6B).

The filter fitting portion 65 forms an integral unit with a filter housing portion 65*a* (refer to FIG. 6B) forming a thin disk-shaped space, the shape of which matches that of the filter 7 which is disposed to close the outlet of the discharge opening 64*a* (refer to FIG. 6B), and a ring supporting portion 65*b* having a cylindrical shape and supporting the filter-securing ring 8.

Second L-shaped grooves 65*c* are formed on the inner circumferential surface of the ring supporting portion 65*b*, and fourth engaging claws 82*a* formed on the filter-securing ring 8 described below are fitted into respective second L-shaped grooves 65*c*. The number of the second L-shaped grooves 65*c* is four, and the second L-shaped grooves 65*c* are formed to be disposed in a constant spacing with each other on the circumferential surface of the ring supporting portion 65*b*.

The filter 7 according to the embodiment is a membrane filter. As described above, the filter 7 closes the outlet of the discharge opening 64*a*. In other words, the filter 7 is disposed on the outside of the discharge opening 64*a*. The filter 7 includes a hydrophilic filter 7*a* and a hydrophobic filter 7*b*, which are arranged in this order from the discharge opening 64*a*.

The hydrophilic filter 7*a* and the hydrophobic filter 7*b* may be selected from products launched in the market. Examples of the hydrophilic filter 7*a* include MF-Millipore (Nihon Millipore K.K.), Durapore (Nihon Millipore K.K.), and Isopore (Nihon Millipore K.K.).

Examples of the hydrophobic filter 7*b* include Mitex (Nihon Millipore K.K.) and Polypropylene Prefilter (Nihon Millipore K.K.).

It should be noted that the filter 7 used in the embodiment should have an outer diameter larger than the inner diameter of the discharge opening 64*a*.

As shown in FIGS. 6A and 6B, the filter-securing ring 8 fixes the filter 7 to the housing 6 (i.e., the conical portion 64). The filter-securing ring 8 has a through hole 81 at a position where the through hole 81 communicates with the discharge opening 64*a* of the conical portion 64 through the filter 7.

The filter-securing ring 8 includes a ring body 82 having a shape substantially same as the inner diameter of the ring supporting portion 65*b* of the filter fitting portion 65 described above, and a flange portion 83 formed on the lower side of the ring body 82 and having a diameter larger than the outer diameter of the ring body 82.

As shown in FIG. 6A, the filter-securing ring 8 further includes: a fitting portion 84 which is deposited on the ring body 82 so that the fitting portion 84 and the ring body 82 form an integral unit, and is fitted into the filter housing portion 65*a* of the housing 6; and a ring-shaped rib 85 vertically disposed on the periphery of an opening of the through hole 81 of the fitting portion 84. The ring-shaped rib 85 presses the filter 7 on the periphery of the outlet of the discharge opening 64*a* (refer to FIG. 6B).

On the circumferential surface of the ring body 82, four of the fourth engaging claws 82*a* are formed to protrude radially outward, and to be disposed in a constant spacing with each other on the circumferential surface of the ring body 82. The fourth engaging claws 82a are formed at positions corresponding to the respective second L-shaped grooves 65c of the ring supporting portion 65b described above, and are fitted into the respective second L-shaped grooves 65c to detachably engage the filter-securing ring 8 with the housing 6.

As shown in FIG. 7, the object-capturing device 1 as described above is formed as follows. The capturing dish 4 is mounted on the shelf portion 63 of the housing 6; the housing 6 is coupled to the cover 3 through the capturing dish 4 using the first L-shaped grooves 61a and the third engaging claws 32; and the through hole 41 of the capturing dish 4 is sealed by the protrusion 33 of the cover 3.

The housing 6 is decoupled from the cover 3 by rotating the housing 6 relative to the cover 3 to disengage the third engaging claws 32 from the first L-shaped grooves 61a.

The filter 7 is disposed in the filter housing portion 65a to close the outlet of the discharge opening 64a of the conical portion 64, and the filter fitting portion 65 is engaged with the filter-securing ring 8 using the second L-shaped grooves 65c and the fourth engaging claws 82a described above. Thereby, the discharge opening 64a of the conical portion 64 communicates with the through hole 81 of the filter-securing ring 8 through the filter 7. As described above, when the filter fitting portion 65 is engaged with the filter-securing ring 8, the filter 7 is pressed by the ring-shaped rib 85 of the filter-securing ring 8, and thereby the filter 7 is disposed on the periphery of the outlet of the discharge opening 64a. Thus, the filter 7 is fixed firmly.

The object-capturing device 1 as described above is used as follows. When the reagents R (refer to FIG. 1) described above are dispensed into the housing 6, the through hole 41 opens to communicate with the internal space 66 which receives the reagents, as shown in FIG. 3. However, before the reagents R are dispensed, the protrusion 33 of the cover 3 seals the through hole 41. The outlet of the discharge opening 64a of the conical portion 64 is closed by the filter 7 which separates microorganisms. As a result, the internal space 66 is a space isolated from the external environment (i.e., a closed space) at least for microorganisms. Consequently, the carrier 5 held on the capturing dish 4 is placed in this closed space.

The object-capturing device 1 as described above other than the filter 7 may be molded with resin, preferably polypropylene.

Method for Using Object-Capturing Device

A method for using the object-capturing device 1 according to the embodiment will be described.

Figure 8:
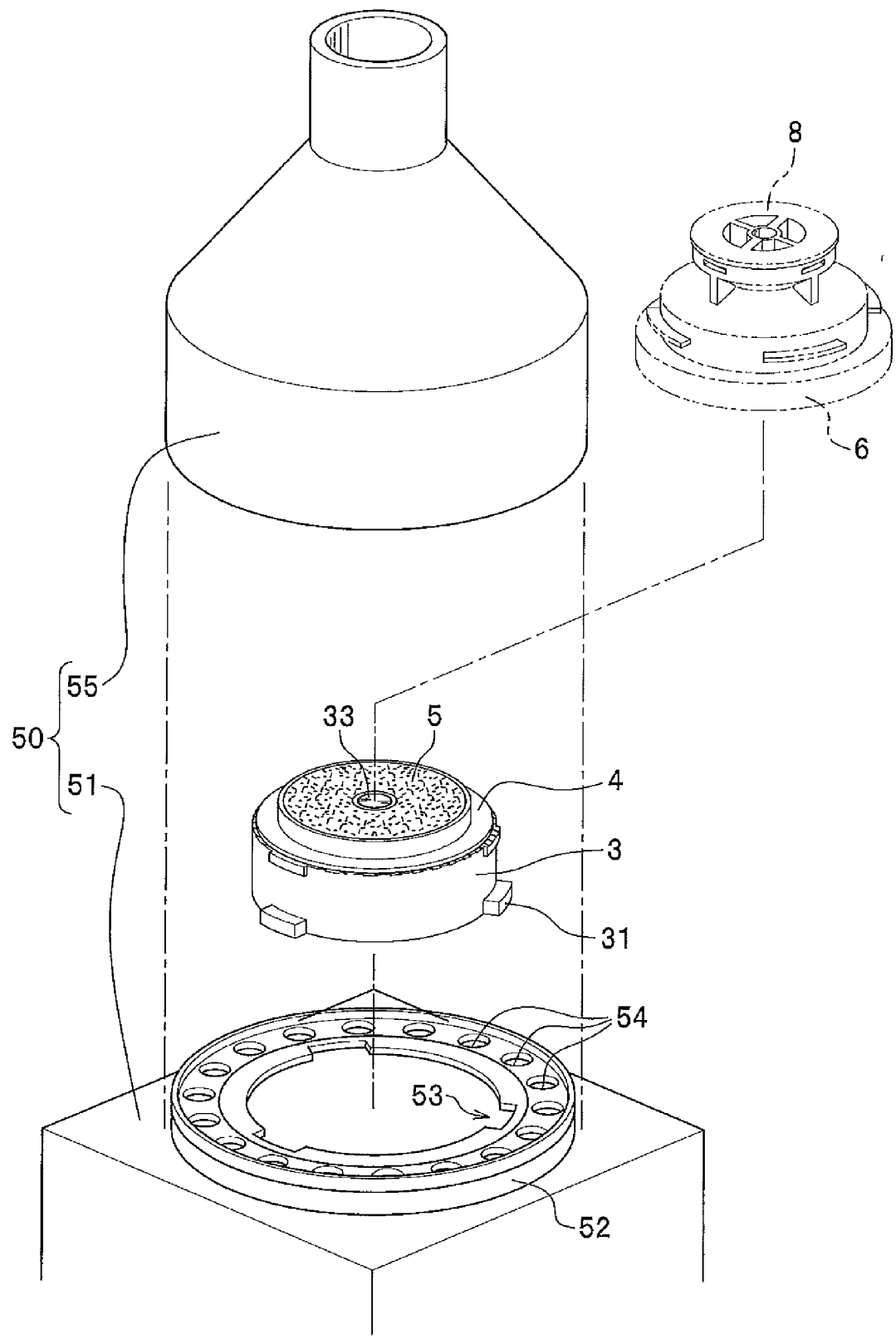
FIG. 8 is a perspective view showing a method for capturing microorganisms using the object-capturing device according to the embodiment of the present invention.

First, a method for capturing microorganisms using the object-capturing device 1 will be described. FIG. 8 referred to below is a perspective view showing the method for capturing microorganisms using the object-capturing device of the present invention.

As shown in FIG. 8, when microorganisms are captured, the object-capturing device 1 is used in such a way that the capturing dish 4 holding the carrier 5 is mounted on the cover 3. In other words, the object-capturing device 1 shown in FIG. 7 is turned upside down and used with the capturing dish 4 left on the cover 3 and with the housing 6 and the filter-securing ring 8 removed. The housing 6 is removed from the cover 3 by rotating the housing 6 relative to the cover 3 to disengage the third engaging claws 32 (refer to FIG. 6A) from the first L-shaped grooves 61a (refer to FIG. 6A) as described above after the cover 3 is located in the pedestal 52 of the air sampler 50 as described below.

The object-capturing device 1 is mounted on the pedestal 52 in a round shape in plan view, which is formed on the upper side of an air sampler body 51 of the air sampler 50. As described above, the pedestal 52 has the engaging cutout portions 53 formed to receive the second engaging claws 31 of the cover 3, and thereby the object-capturing device 1 is located in a center portion of the pedestal 52.

FIG. 8 shows suction openings 54 of the air sampler body 51, and a nozzle head 55 of the air sampler 50.

According to the method for capturing microorganisms, the housing 6 and the filter-securing ring 8 which form an integral unit are removed to expose the carrier 5 of the object-capturing device 1 mounted in the pedestal 52, and the nozzle head 55 is placed over the pedestal 52, as shown in FIG. 8. The process of exposing the carrier 5 corresponds to "the step of exposing the carrier" in the claims.

A fan (not shown) disposed in the air sampler body 51 is activated, and the air is sucked through the suction openings 54. Then, air flow is injected to the carrier 5 from multiple micro nozzles (not shown) provided in the nozzle head 55. As a result, microorganisms carried in the air injected to the carrier 5 are captured by the carrier 5. In other words, microorganisms are captured with the carrier 5 directed upward.

As shown in FIG. 8, the protrusion 33 of the cover 3 seals the through hole 41 (refer to FIG. 7) of the capturing dish 4. Thus, the surface of the capturing dish 4 on the side of the carrier 5 is flush with the bottom of the protrusion 33. This reduces disturbance of the received air flow. Consequently, the carrier 5 is capable of capturing microorganisms efficiently.

When the air sampler 50 sucks a predetermined amount of the air, the process of capturing microorganisms with the object-capturing device 1 ends. This capturing process corresponds to "the step of capturing the object" in the claims.

When this capturing process ends, the housing 6 and the filter-securing ring 8 which form an integral unit are fitted to the cover 3 again, and the object-capturing device 1 returns back to the state shown in FIG. 7. This process corresponds to "the step of placing the housing again over the capturing dish to cover the carrier" in the claims.

A method for using the object-capturing device 1 in the microorganism counting apparatus 10 which counts the captured microorganisms will be described.

When the capturing process described above ends, the object-capturing device 1 as shown in FIG. 7 is carried by a user into the microorganism counting apparatus 10, as described above (refer to FIG. 2).

As described above, the object-capturing device 1 is mounted on the mounting unit 102, and the cover 3 is removed from the housing 6 by the user (refer to FIG. 3).

FIGS. 9A1 to 9A4 are cross-sectional views of the object-capturing device, showing the method for using the object-capturing device in the microorganism counting apparatus. FIGS. 9B1 to 9B4 are enlarged schematic diagrams showing the vicinity of the filter in the case of FIGS. 9A1 to 9A4.

FIGS. 9B1 to 9B4 show microorganisms B and ATPs. However, the sizes of actual microorganisms are as small as in the order of micrometer, and the sizes of actual ATPs are as small as that of a molecule. Accordingly, FIGS. 9B1 to 9B4 shows no relative sizes of a microorganism and an ATP.

When the temperature of the carrier 5 is raised in Step S201 (refer to FIG. 4) as described above, the carrier 5 held on the capturing dish 4 solates and falls down onto the conical portion 64 of the housing 6 as shown in FIG. 9A1. In this step, the microorganisms B captured with the air sampler 50 (refer to FIG. 8) are retained with the carrier 5 on the filter 7 as shown in FIG. 9B1.

When the hot water HW is injected into the housing 6 in Step S202 (refer to FIG. 4) as described above, the carrier 5 further solates and is diluted by the hot water. The filter 7 includes the hydrophobic filter 7b on the lower side thereof as shown in FIG. 9A2. Thus, the hot water HW containing the diluted carrier 5 is retained in the housing 6. The microorganisms B are retained in the hot water HW containing the diluted carrier 5 on the filter 7. FIG. 9A2 also shows the capturing dish 4, and the conical portion 64 (The same reference number denotes the same element throughout the following views.)

When the contents in the housing 6 are filtered in Step S203 (refer to FIG. 4) as described above, the hot water HW containing the diluted carrier 5 in the housing 6 (refer to FIG. 9A2) is discharged as shown in FIG. 9A3. In this step, the microorganisms B in the hot water HW containing the diluted carrier 5 are separated and held by the filter 7 as shown in FIG. 9B3.

As shown in FIG. 9B3, the filter 7 according to the embodiment has a double layer structure of the hydrophilic filter 7a and the hydrophobic filter 7b. Unlike a filter including only a hydrophilic filter, which is used in conventional ATP methods, the hydrophobic filter 7b enables liquid to be retained on the filter unless the liquid is sucked or pressure-filtered. This enables reaction with reagent, such as ATP extraction, to be performed on the filter 7.

The ATP eliminating reagent is dispensed into the housing 6 in Step S206 (refer to FIG. 4) as described above, and then the ATP extracting reagent is dispensed into the housing 6 in Step S210 (refer to FIG. 4) as described above.

These processes of dispensing the reagents correspond to "the step of injecting a reagent into the housing" in the claims.

In the housing 6, into which the ATP extracting reagent is injected in Step S210 (refer to FIG. 4) as described above, ATP extracted solution EX is retained as shown in FIG. 9A4. As shown in FIG. 9B4, the ATP extracted solution EX contains ATPs, the amount of which corresponds to the number of the microorganisms B.

The ATP extracted solution EX shown in FIG. 9B4 is dispensed into the luminescence-test tube 107a (refer to FIG. 1) in Step S211 (refer to FIG. 4) as described above, and then the process sequence of the method for using the object-capturing device 1 ends.

According to the object-capturing device 1 and the using method thereof as described above, microorganisms are captured with the carrier 5 directed upward, and then the carrier 5 is directed downward to contact the microorganisms with the reagents through the through hole 41.

Accordingly, the carrier 5 directed upward facilitates the capturing of the microorganisms. When the reagents are contacted with the microorganisms, that is, the microorganisms are detected, the carrier 5 is directed downward, and thereby the capturing dish 4 serves as a cover of the carrier 5. For example, this prevents the carrier 5 from being contaminated with, for example, dust and microbes falling from above.

According to the object-capturing device 1 and the using method thereof, before the object-capturing device 1 is mounted in the air sampler 50, and during the time after the microorganisms are captured using the air sampler 50 and before the captured microorganisms are carried into the microorganism counting apparatus 10, the carrier 5 is placed in the closed space in the housing 6. As a result, the carrier 5 is prevented from being contaminated with substances which are disturbance factors for the counting of the microorganisms, unlike a conventional capturing device with an exposed carrier, such as the device disclosed in Japanese Patent Application Laid-Open No. 2009-131186.

Consequently, the object-capturing device 1 and the using method thereof enable more accurate counting of the microorganisms captured at a test site.

According to the object-capturing device 1 and the using method thereof, when the microorganisms are contacted with the reagents R using the microorganism counting apparatus 10, the reagents R are dispensed into the housing 6 through the through hole 41 of the capturing dish 4. This minimizes the communication between the inside and the outside of the housing 6. As a result, the inside of the housing 6 is prevented from being contaminated with substances which are disturbance factors for the counting of the microorganisms.

According to the object-capturing device 1 and the using method thereof, the housing 6 has the discharge opening 64a through which the contents are discharged, and the discharge opening 64a has the filter disposed thereon to separate and hold microorganisms. Thereby, the microorganisms may be contacted with the reagents R in the housing 6. Consequently, the object-capturing device 1 and the using method thereof dramatically reduce the disturbance factors for the counting of the microorganisms, unlike a conventional capturing device, such as the device disclosed in Japanese Patent Application Laid-Open No. 2009-131186, which is used in a way such that microorganisms are extracted from the capturing device and the extracted microorganisms are contacted with reagents for counting.

According to the object-capturing device 1 and the using method thereof, the filter 7 has a double layer structure of the hydrophilic filter 7a and the hydrophobic filter 7b. Thereby, reaction of reagents with recovered microorganisms may be performed on the filter 7, unlike a filter used in the conventional ATP methods, which includes only a hydrophilic filter.

According to the object-capturing device 1 and the using method thereof, the cover 3 has the second engaging claws 31 formed on the opposite side of the housing 6 to engage with the air sampler. To expose the carrier 5, the housing 6, which is fixed with the cover 3 to form an integral unit as shown in FIG. 5, is grasped by hands, the cover 3 is placed into the air sampler 50 as shown in FIG. 8, and then the housing 6 is removed from the cover 3. In other words, when the carrier 5 is exposed, the capturing dish 4 holding the carrier 5 is not touched by hands. Consequently, the object-capturing device 1 and the using method thereof surely prevent the carrier 5 from being contaminated with substances which are disturbance factors for the counting of the microorganism.

According to the object-capturing device 1 and the using method thereof, after the object-capturing device 1 is mounted on the mounting unit 102, when the cover 3 is removed from the housing 6 by a user, the capturing dish 4 is turned upside down relative to the state at the time when placed in the air sampler, and thereby the carrier 5 faces toward the internal space 66. This surely prevents the contamination of the carrier 5. This advantage may be achieved regardless of the type or the number of the filter 7, such as the hydrophilic filter 7a or the hydrophobic filter 7b described above.

The embodiment of the present invention has been described. The present invention is not limited to the embodiment described above, and various modifications can be made.

According to the embodiment described above, the microorganisms captured with the object-capturing device 1 are counted in the microorganism counting apparatus 10. Instead of using the microorganism counting apparatus 10, the reagents R may be manually dispensed into the housing 5 to count the microorganisms by the ATP method.

The present invention is applicable to spore-forming bacteria such as *Bacillus subtilis*. In this case, examples of the reagents described above may include a vegetative cell conversion reagent, such as amino acid and sugar.

According to the embodiment described above, the ATP method is used to count microorganisms. Instead, the microorganisms may be counted based on the fluorescence produced when substances in a living body, such as DNA, RNA, and NAD, which are extracted from the microorganisms, are irradiated with excitation light.

In the case where the object-capturing device 1 is used to capture and count gram negative bacilli, the counting may be made based on endotoxin contained in the cell membrane of gram negative bacilli. In other words, microbes may be counted based on luminescence intensity resulting from the limulus test on the endotoxin.

The microorganisms may be counted by recovering the microorganisms from the filter 7 and culturing the recovered microorganisms.

What is claimed is:

1. An object-capturing device comprising:
   a capturing dish having a first side and a second side opposite the first side, the capturing dish having ring-shaped ribs disposed on the first side at an outer circumference of the first side and an inner circumference of the first side for holding a carrier, which captures an object and is made of a material that undergoes a phase transition from gel to sol as the temperature of the carrier is raised, between the ring-shaped ribs on the first side of the capturing dish, wherein the first side is directed upward when the carrier captures the object and directed downward when the object is being detected; and
   a housing disposed relative to the capturing dish to cover the carrier, wherein the housing and the capturing dish are arranged to provide a space formed between the first side of the capturing dish and the housing when the object is being detected, the housing having a discharge opening for discharging the carrier in a form of a sol out of the housing;
   a heater to raise the temperature of the carrier; and
   a filter separating the object disposed on the outside of the discharge opening, filter comprising a hydrophilic filter and a hydrophobic filter disposed in this order from the discharge opening,
   wherein the capturing dish has a through hole extending through the first side and the second side of the capturing dish connecting the space formed between the first side of the capturing dish and the housing with the outside of the housing.

2. The object-capturing device according to claim 1, further comprising:
   a cover mounted on the second side of the capturing dish and detachably fitted to the housing,
   wherein the cover has an engaging portion on the opposite side of the housing, and the engaging portion engages the cover with a capturing apparatus which captures the object with the carrier held by the capturing dish.

* * * * *